(12) United States Patent
Drevik (10) Patent No.: US 8,926,578 B2
(45) Date of Patent: Jan. 6, 2015

(54) MALE INCONTINENCE PROTECTOR (75) Inventor: Solgun Drevik, Mölnlycke (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 13/805,890

(22) PCT Filed: Jun. 24, 2010

(86) PCT No.: PCT/SE2010/050730
§ 371 (c)(1),
(2), (4) Date: Jan. 24, 2013

(87) PCT Pub. No.: WO2011/162657
PCT Pub. Date: Dec. 29, 2011

(65) Prior Publication Data
US 2013/0138070 A1    May 30, 2013

(51) Int. Cl.
*A61F 13/15*   (2006.01)
*A61F 13/20*   (2006.01)
*A61F 13/471*  (2006.01)
*A61F 13/56*   (2006.01)

(52) U.S. Cl.
CPC ........... *A61F 13/471* (2013.01); *A61F 13/5611* (2013.01)
USPC ....... 604/385.01; 604/356; 604/347; 604/349

(58) Field of Classification Search
CPC . A61F 13/15203; A61F 5/453; A61F 13/471; A61F 13/533; A61F 13/4915; A61F 5/4408
USPC .............................. 604/385.01, 349, 346–347
See application file for complete search history.

(56) References Cited

U.S. PATENT DOCUMENTS

2003/0130643 A1* 7/2003 Drevik et al. ............ 604/385.31
2004/0162537 A1   8/2004 Manasek
2009/0182297 A1   7/2009 Hedström et al.

FOREIGN PATENT DOCUMENTS

| DE | 20 2007 005 479 | 8/2007 |
|---|---|---|
| EP | 1 395 216 | 3/2004 |
| RU | 2288686 | 12/2006 |
| WO | 02/087484 | 11/2002 |
| WO | 2006/123973 | 11/2006 |
| WO | 2007/061341 | 5/2007 |
| WO | 2007/073254 | 6/2007 |
| WO | 2009/061241 | 5/2009 |
| WO | 2010/039068 | 4/2010 |

* cited by examiner

*Primary Examiner* — Melanie Hand
*Assistant Examiner* — Aundria Hairell
(74) *Attorney, Agent, or Firm* — Drinker Biddle & Reath LLP (57) ABSTRACT

A male incontinence protector includes a longitudinal direction and a transverse direction, a front end portion with a front end edge, and a rear end portion with a rear end edge. The front end portion has greater maximum extension in the transverse direction than the maximum extension of the rear end portion in the transverse direction. The male incontinence protector further includes side edges extending between the front end edge and the rear end edge, a garment-facing surface, and a wearer-facing surface. The incontinence protector has a tendon engagement member arranged in the rear end portion.

16 Claims, 8 Drawing Sheets

MALE INCONTINENCE PROTECTOR

CROSS-REFERENCE TO PRIOR APPLICATION

This application is a §371 National Stage Application of PCT International Application No. PCT/SE2010/050730 filed on Jun. 24, 2010, which is incorporated herein in its entirety.

TECHNICAL FIELD

The disclosure pertains to a male incontinence protector having a longitudinal direction and a transverse direction, a front end portion with a front end edge and a rear end portion with a rear end edge, the front end portion having greater maximum extension in the transverse direction than the maximum extension of the rear end portion in the transverse direction, side edges extending between the front end edge and the rear end edge, a garment-facing surface and a wearer-facing surface.

BACKGROUND

The disclosure is particularly directed to incontinence protectors intended for use by men suffering from relatively mild incontinence problems involving small to moderate amounts of urine leakage. Such incontinence protectors range from thin shields that may only capture a few drops of urine to larger devices that may absorb and contain several hundred milliliters of urine. Urine incontinence and its causes are different between men and women. Many men who suffer from prostate problems also suffer from light incontinence. Due to the anatomical differences between men and women, and the differences in the nature of the incontinence, incontinence guards have been specially designed for male users.

A male incontinence protector is shown in international patent application WO 2007/061341 A1. It has a generally triangular shape with a wider front part and a narrow rear part. Such an incontinence protector is fitted inside a wearer's underwear and is shaped and sized to enclose the wearer's penis and extend beneath the scrotum. Further examples of incontinence protectors that have been shaped and configured to conform to the male anatomy are found in international patent application WO 2009/061241 A1 and international patent application WO 2006/123973 A1.

The incontinence protectors in WO 2007/061341 A1 and WO 2009/061241 A1 are of a kind that is attached inside the wearer's undergarment. The attachment is achieved by means of adhesive arranged on the surface of the incontinence protector which is facing the wearer's undergarment when the incontinence protector is being worn.

When attaching the incontinence protector to the undergarment, there is a risk that the wearer places the protector in a less suitable position in relation to the body, such as slightly to one side or too far to the rear or to the front of the undergarment. Such misplacement of the incontinence protector will increase the risk that urine escapes out of the incontinence protector resulting in highly undesirable leakage. Moreover, when worn, the incontinence protector will tend to shift with the movements of the undergarment as the wearer moves, further increasing the risk of leakage. Elderly males who constitute a major proportion of the men experiencing incontinence problems tend to choose loosely fitting undergarments implying that an incontinence protector fastened to such a garment will be located at a distance from the wearer's body so that a gap is formed between the incontinence protector and the wearer's body. Leakage of urine through the gap between the incontinence protector and the wearer's body is almost unavoidable in those cases.

In order to improve body contact, the incontinence protector in WO 2006/123973 A1 is designed with a fastening arrangement taking the form of a pocket into which the penis may be inserted in order to hold the incontinence protector against the wearer's body. Although leakage may be minimized with this arrangement many wearers dislike the feeling of constraint and tightness that the pocket evokes.

Accordingly, there still remains a strong need for an improved arrangement for holding a male urine incontinence protector securely and comfortably in place during wearing.

SUMMARY

The present disclosure provides a urine incontinence protector for males who suffer from mild to moderate incontinence. The incontinence protector solves the problem of securely and comfortably retaining the incontinence protector in close contact with the body of the wearer.

The male urine incontinence protector has a longitudinal direction and a transverse direction, a front end portion with a front end edge and a rear end portion with a rear end edge, the front end portion having greater maximum extension in the transverse direction than the maximum extension of the rear end portion in the transverse direction, side edges extending between the front end edge and the rear end edge, a garment-facing surface and a wearer-facing surface. The incontinence protector includes tendon engagement means arranged in the rear end portion of the incontinence protector.

When the incontinence protector is being used, the tendon engagement means will be placed behind the wearer's scrotum, in the groin and in abutting contact with two muscle groups extending down on the insides of the thighs on each side of the groin. In this manner, the incontinence protector will be held securely in place in a correct position against the wearer's body. The tendon engagement means will be in contact with and optionally pressing against the tendons at each side of the groin so that the incontinence protector will be held clamped between the wearers legs and kept centred with respect to a bisecting plane through the wearer's body dividing the body into left and right halves. Hence, sideways movement of the incontinence protector will be counteracted in this manner. The tendon engagement means will also counteract longitudinal movement of the incontinence protector as forward and/or rearward widened portions of the tendon engagement means become hooked against the tendons in the groin and thereby restrict unwanted longitudinal displacement of the incontinence protector.

The tendon engagement means is a structure or a component in the incontinence protector that is immediately recognised as being different in its primary function from structures and components such as a topsheet, a backsheet and an absorbent core or a fastener for attaching the incontinence protector to an undergarment. Accordingly, the tendon engagement means is clearly delimited from surrounding portions of the incontinence protector and is readily identified as a special structure or component in the incontinence protector.

The tendon engagement means may comprise or consist of a stiffened portion of one or more of the absorbent core, the backsheet, the topsheet or some other component in the incontinence protector. Examples of such stiffened portions are compressed lines and compressed areas, areas containing additional layers of material and/or material that has been treated to have increased stiffness such as by impregnation, bonding or melting. Furthermore, the tendon engagement means may comprise or consist of one or more tendon abutment elements that are stiffening inserts of plastic, metal, wood, fibreboard, paper, etc. Stiffening inserts that are activated when the incontinence protector is being worn may also be used. One example of a stiffening insert that is activated when the incontinence protector is worn is an insert that becomes stiff upon wetting such as that disclosed in international patent publication WO 2007/073254 A1.

During wearing of the incontinence protector, at least a part of the tendon engagement means on each longitudinal side of the incontinence protector will be in abutting contact with the insides of the wearer's thighs in the groin. The tendon engagement means preferably has a sufficient width and is sufficiently stiff or rigid to hook and/or press against the insides of the wearer's thighs. As the wearer moves and changes body position, the hooking and clamping effect arising from the contact between the tendon engagement means and the wearer's body provides the incontinence protector with an improved ability of staying in place during wearing of the incontinence protector as compared with a corresponding incontinence protector without a tendon engagement means. The improved retention of the incontinence protector in the crotch of the wearer provided by the tendon engagement means is obtained without causing any discomfort to the wearer and will have a direct and positive effect on the leakage security of the incontinence protector.

It is highly desirable that the functional width of the tendon engagement means in the rear end portion is adapted to the anatomy of the wearer, so that the article may be securely and comfortably held in place between the wearer's legs without wrinkling, chafing or exerting undue pressure on the sides of the wearer's thighs. Measurements have shown that all humans have a space-limiting narrow area in the groin, the narrow area being transversely defined by the distance between the tendons of two muscle groups which extend from the inside of the base of the pelvis down along each thigh. The distance between the tendons has been found to be surprisingly similar for all individuals and to be independent of body shape and weight. Thus, although the apparent distance between the thighs of a person may vary due to different body weight in different individuals, the distance between the tendons in the groin is the same independently of whether the person is thin, of normal weight, or overweight. It has been found that the factor which ultimately determines whether a wearer of an incontinence protector experiences uncomfortable pressure against the tendons in the groin or chafing against the insides of the thighs is if a stiffened part of the incontinence protector that is placed in the narrow area has a width which considerably exceeds the distance between the muscle groups in the groin area. This distance has been found to be between approximately 30 mm and 35 mm. Furthermore, it has been shown that when a stiffened part of the incontinence protector having a width exceeding 40-45 mm is placed in the narrow area of the groin, the incontinence protector will be perceived as being uncomfortable to wear by a majority of wearers. However, the incontinence protector is generally not considered to be uncomfortable if it a stiffened part merely presses against or displaces fatty tissue which may be present in the groin area.

In particular embodiments, in order for the tendon engagement means to firmly hook against the tendons in the groin area and still fit comfortably in the parts of the groin located forward and rearward of the narrowest part between the space limiting muscle groups, it is preferred that the tendon engagement means has a maximum extension in the transverse direction of from 40 mm to 70 mm, preferably from 45 mm to 60 mm.

As used herein, the front end portion of the incontinence protector is the part of the incontinence protector located longitudinally in front of a transverse centre line through the incontinence protector. Correspondingly, the rear end portion is the part of the incontinence protector located longitudinally rearward of the transverse centre line. Consequently, the front end portion is the front half of the incontinence protector and the rear end portion is the rear half of the incontinence protector.

The male incontinence protector may be designed with its front end portion having a considerably greater maximum width near the front end edge than the width of the rear end portion near the rear end edge in order to conform to the shape and curvature of the male anatomy in the genital area. Accordingly, the incontinence protector may have a generally triangular shape or a saddle shape with an elongate narrow portion at the rear of the incontinence protector.

The incontinence protector will usually have a liquid barrier layer, or backsheet, arranged on the garment-facing surface and a liquid permeable layer, or topsheet, arranged on the wearer-facing surface. An absorbent core may be placed between the backsheet and the topsheet, as is conventional in the art. The backsheet and/or the topsheet may be formed integral with the absorbent core or may be separate components in the incontinence protector.

A backsheet may comprise or consist of any suitable liquid barrier material as known in the art such as a polymeric film, a hydrophobic nonwoven layer or a liquid impermeable laminate of two or more layers. The liquid barrier layer may be formed as a coating on a liquid permeable layer or on an absorbent core. In a particular embodiment, the liquid barrier layer is liquid impermeable but may be breathable, allowing air and vapour to pass through the layer, thus improving wearer comfort and making the protector feel less warm and damp when worn. It is also common in the art to provide the garment-facing surface of the backsheet with a textile or textile-like material. A textile or textile-like surface may be obtained by arranging fibres or a nonwoven web on the garment-facing surface of the backsheet or by embossing or other surface modifying treatment of the garment-facing surface of the backsheet. A surface having a textile feel will be perceived as more comfortable when it comes into contact with the skin of a wearer, as is likely to occur at the edges of the incontinence protector and when handling the incontinence protector. Moreover, a textile appearance is beneficial in that it makes the incontinence protector more like a normal undergarment.

The topsheet may be any suitable liquid permeable material as known in the art including perforated and non-perforated textiles such as woven or nonwoven materials, perforated polymeric film, scrim, etc. The liquid permeable layer may include laminates and combinations of materials to improve liquid acquisition, liquid transport and wetback, as known in the art.

In its simplest form, the incontinence protector may be formed from a single layer of material serving as a mere drip catcher or panty shield for wearers suffering from an inability of completely emptying the urea after urination. An incontinence protector of this kind need not have any actual absorption capacity and it may suffice that the small amounts of urine caught by the protector stays on the wearer-facing surface of the incontinence protector. For small to moderate liquid volumes, the incontinence protector may be formed from a combined topsheet/absorption material and a backsheet.

For larger expected liquid volumes, the incontinence protector will usually have an inner, wearer-facing liquid permeable layer, an outer liquid barrier layer that is liquid impermeable or at least resistant to liquid penetration and an absorbent core enclosed between the liquid permeable layer and the liquid barrier layer.

The incontinence protector may be provided with elastic means arranged to create a three-dimensional curve-shape in the incontinence protector. To this end, pre-stretched elastic elements may be attached along the side edges of the incontinence protector. Due to the generally tapering shape of the incontinence protector, the elastic elements will curve the incontinence protector into a J-shape as the bending resistance in the rear part of the incontinence protector decreases with the width of the incontinence protector.

When the incontinence protector is worn, it is placed against the wearer's body in the groin area with the wearer-facing surface in direct contact with the wearer's body. The front end edge is located towards the wearer's abdomen and the rear end edge and the tendon engagement means are placed behind the scrotum. When applied to the body of the wearer, the incontinence protector assumes a curved configuration with the front end portion extending downward from the front end edge and the rear end portion extending from the front end portion downward and rearward between the wearer's legs to cover the wearer's penis and scrotum.

The incontinence protector is held securely and comfortably in place in close contact with the wearer's body during wearing of the incontinence protector due to the provision of the tendon engagement means. However, if desired, the tendon engagement means may be supplemented with additional fastening means such as adhesive fasteners or mechanical fasteners, as known in the art. In certain embodiments, such additional fasteners are placed on the front portion of the incontinence protector, and in particular, near the front end edge of the incontinence protector in order to minimise interference with the body-conforming retention provided by the tendon engagement means. Additional fastening means in the form of body adhesive may also be used to enhance the body-conforming and retaining effect of the tendon engagement means. Body adhesives are skin-compatible adhesives that may be used to attach the incontinence protector directly to a wearer's skin.

In particular embodiments, the tendon engagement means may have an extension in the longitudinal direction of the incontinence protector of up to 60 mm, such as 3 mm to 50 mm. In its simplest version, the tendon engagement means may be a narrow rigid transverse element such as a compression line or narrow rigid insert. In more complicated embodiments, the tendon engagement means may include one or more parts having the same or different widths in different parts of the tendon engagement means and may include parts being spaced apart in the length direction of the incontinence protector within the area of the tendon engagement means.

The width restricted area in the groin normally has a length of 5-15 mm. Hence, if present within this area, the tendon engagement means may preferably not have a width exceeding 40 mm and preferably not exceeding 35 mm. At the same time, the tendon engagement means preferably has at least one part intended to be positioned rearward or forward of the width restricted area in the groin where the width of the tendon engagement means exceeds the width of the width restricted area in the groin.

In accordance with certain embodiments, the tendon engagement means may be placed in a part of the rear end portion extending up to 70 mm from the rear end edge and preferably up to 50 mm from the rear end edge. By arranging the tendon engagement means in the rearmost part of the rear end portion, the incontinence protector will be placed completely forward of the wearer's anus.

The tendon engagement means may include at least one compressed groove. The compressed groove may be formed in one or more layers in the incontinence protector and may be formed in any structure of the incontinence protector such as in a liquid permeable topsheet, an absorbent core or in both topsheet and core. It is also conceivable to form a compressed groove in a bulky liquid barrier such as in a foam barrier material. The purpose of the compressed groove is to increase stiffness in the material within the area of the groove and make the material in the compressed area more resistant to lateral compression than parts of the material surrounding the compressed groove. A compressed groove may be visually identified as a thinner, generally elongate, sunken portion in a surface of a material. The compressed groove may be further recognised by having a denser fibrous structure, smaller pores, collapsed cells, etc. than the surrounding parts of the material.

The tendon engagement means may include two intersecting compressed grooves. The grooves may be arranged in an X-shape in the rear end portion of the incontinence protector whereby the X-shape enhances the hooking effect created between the tendon engagement means and the tendons of the muscle groups in the wearer's groin. A similarly enhanced hooking effect may be obtained with grooves arranged in a degenerated X-shape resembling arrowheads ><directed with their points towards the longitudinal centreline of the incontinence protector. Further groove configurations such as a Y-shape, V-shape, inverted Y-shape and V-shape, a shape resembling the Greek letter Ξ or grooves arranged in the shape of the letter H having slightly curved legs are also contemplated in different embodiments of the invention.

The tendon engagement means may consist of or comprise an absorbent or non-absorbent tendon abutment element. The abutment element is a separate component in the incontinence protector and may be manufactured from a thermoplastic material such as polymeric foam. Examples of suitable foams are polyolefinic foams e.g. polyethylene foam or polypropylene foam or foams made from polyester, polybutylene, ethylene vinyl acetate, polyurethane, thermobondable cellulose, latex silicone elastomerics and others. Other suitable materials for the abutment element are fibers, films or sheets of cellulose, rayon, nylon, polyester, stiffened cotton, polyethylene, vinyl acetate, plastic heavy-weight paper such as cardboard, coated paper, or a combination or laminate of these or other materials. When properly dimensioned in the transverse direction, the abutment element will fit perfectly in the narrow space between the muscle tendons in a wearer's groin and may be made of extremely stiff and unyielding materials without causing discomfort to the wearer. Accordingly, the abutment element may be made from materials such as hard plastic, metal and wood.

The tendon abutment element may be placed anywhere in the thickness direction or z-direction of the rear end portion, such as on the garment-facing surface, the wearer-facing surface or between the garment-facing surface and the wearer-facing surface.

The incontinence protector may have a raised portion, or hump, on the wearing-facing side of the rear end portion. The raised portion may be an element that is separate and functions independently from the tendon engagement means. Alternatively, the raised portion may be an element of the tendon engagement means or may constitute the tendon engagement means.

In addition to the tendon engagement means, the incontinence protector may include side edge shaping means arranged along the side edges. The side edge shaping means are arranged to create a cup-shape in the incontinence protector, at least in the transverse direction and optionally also in the longitudinal direction. A transverse shaping means may be arranged in the front end portion of the incontinence protector, and in particular along the front end edge of the incontinence protector. If the incontinence protector is provided with side edge shaping means, the transverse shaping means may be arranged between the side edge shaping means and may be formed continuously with the side edge shaping means or as a separate element. In particular embodiments, the transverse shaping means are stiffened structures that act to keep the front end edge stretched out when the incontinence protector is worn and contribute to the formation of a cup-shape in the front end portion of the incontinence protector.

The side edge shaping means may include grooves formed on the wearer-facing side of the incontinence protector. The grooves may be compressed grooves as herein disclosed or may be channels that have been formed by removal of material and may be present in a topsheet only or in a topsheet and an absorbent core positioned beneath the topsheet. The grooves constitute hinge means about which side edge portions located between the grooves and the side edges may be folded towards the wearer-facing surface of the incontinence protector to form raised side walls along the side edges of the incontinence protector. Furthermore, the side edge shaping means may be arranged in side flaps formed by cover materials extending laterally outside of an absorbent core.

The side edge shaping means may include absorbent or non-absorbent elongate shaping elements extending along the side edges of the incontinence protector. The shaping elements are arranged to increase the stiffness and bending resistance of a portion of the incontinence protector located along each of the side edges. Similar to shaping means including grooves, when arranged at a distance from the side edges the elongate shaping elements will facilitate bending of the portion of the incontinence protector located between the elongate shaping element and the side edge along the edge of the elongate shaping element. The side edge shaping means may be combined with side elastic elements to achieve controlled deformation and shaping of the incontinence protector.

The side edge shaping means may be formed in the same manner as the tendon engagement means located in the rear end portion of the incontinence protector, such that the side edge shaping means is of the same type as the tendon engagement means. Accordingly, if the tendon engagement means includes one or more compressed grooves, or compressed areas, the side edge shaping means may also be formed as compressed structures and may even be formed as continuous extensions of compressed structures in the tendon engagement means. Likewise, if the tendon engagement means is a stiffening insert, the side edge shaping means may also be formed by applying stiffening material along the side edges.

Accordingly, the side edge shaping means and the tendon engagement means in the rear end portion of the incontinence protector may comprise or consist of a coherent absorbent insert having a base portion placed in the rear end portion of the incontinence protector and two diverging leg portions extending along the side edges of the incontinence protector.

BRIEF DESCRIPTION OF THE DRAWINGS

Embodiments of the invention will be described in greater detail below with reference to the figures shown in the appended drawings.

FIGS. 5 a-c show alternative shapes for a tendon engagement means according to embodiments of the invention;

DETAILED DESCRIPTION OF PREFERRED EMBODIMENTS

Figure 1:
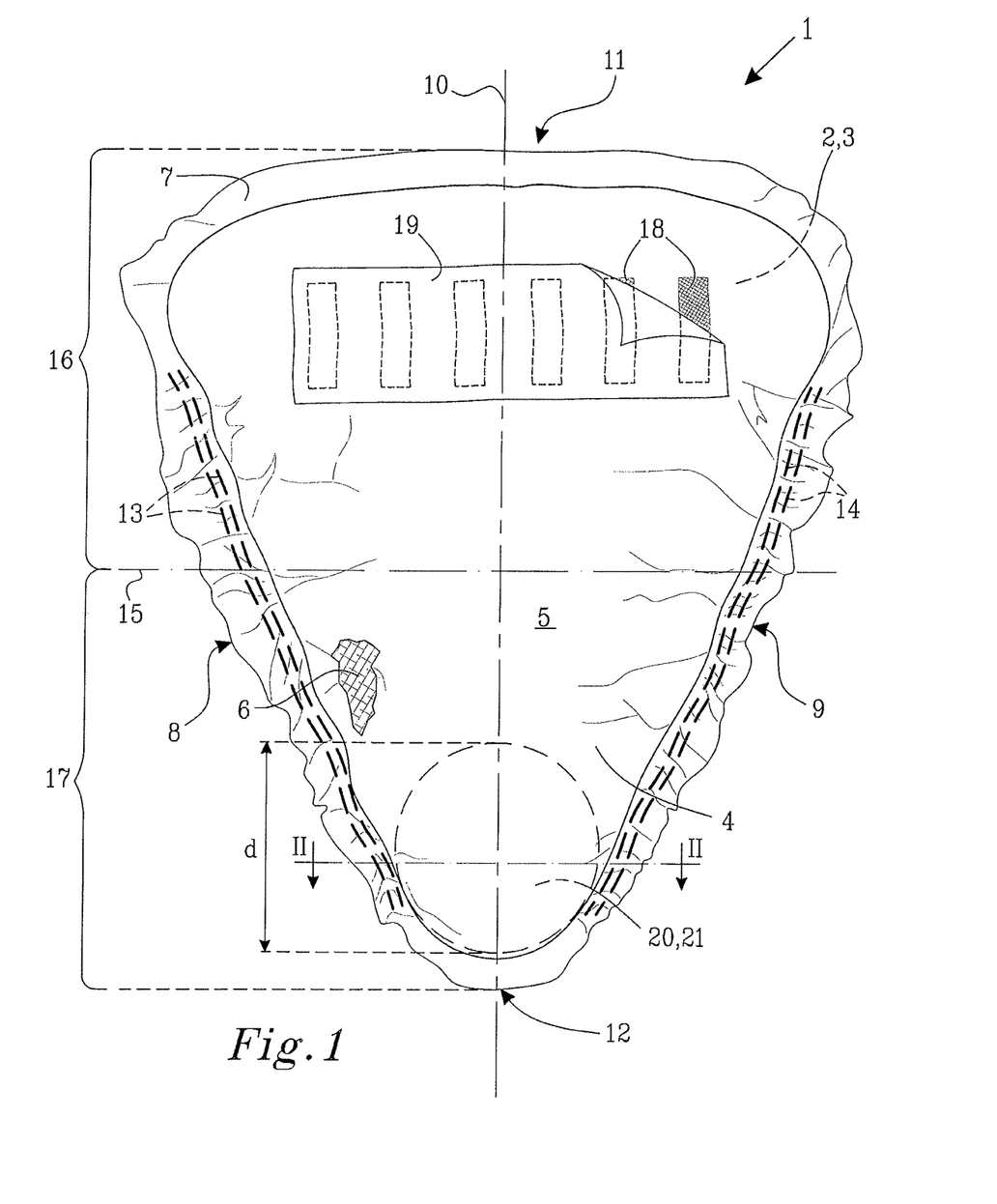
FIG. 1 shows an incontinence protector according to an embodiment of the invention, seen from the side which will be facing the undergarment when the incontinence protector is being worn.

A male urine incontinence protector according to a first illustrative embodiment is shown in FIGS. 1-4. FIG. 1 shows the incontinence protector 1 in a flattened-out state and seen from the side of the incontinence protector 1 that is intended to be facing towards a wearer's undergarment when the incontinence protector 1 is being worn.

The incontinence protector 1 includes a liquid-permeable topsheet 2, disposed at the surface 3 of the incontinence protector 1 which is the surface intended to be facing a wearer of the incontinence protector 1 when the incontinence protector 1 is being worn, a backsheet 4 disposed at the surface 5 of the incontinence protector 1 which is the surface intended to be facing the undergarment of a wearer of the incontinence protector 1 when the incontinence protector 1 is being worn, and an absorbent core 6, enclosed between the topsheet 2 and the backsheet 4.

The topsheet 2 and the backsheet 4 of the incontinence protector in FIGS. 1-4 extend together laterally outside of the absorbent core 6 along the whole circumference of the absorbent core 6 and are connected to each other in an edge join 7 outside the absorbent core 6. The edge join 7 may be formed in any suitable manner as known in the art such as by means of adhesive, ultrasonic bonding, thermobonding, stitching, etc. Alternative arrangements without an edge join formed in covering material extending outside the peripheral edges of an absorbent core are of course also conceivable.

The topsheet 2 may include any material which is suitable for the purpose. Examples of commonly found topsheet materials are nonwoven materials, perforated plastic films, plastic or textile meshes, and liquid permeable foam layers. Topsheet materials which are constituted by continuous thin fibers extending substantially in the longitudinal or transverse direction of the product are also known. Laminates including two or more topsheet materials are also commonly employed, as are topsheets including different materials within different parts of the liquid permeable wearer-facing surface.

Figure 2:
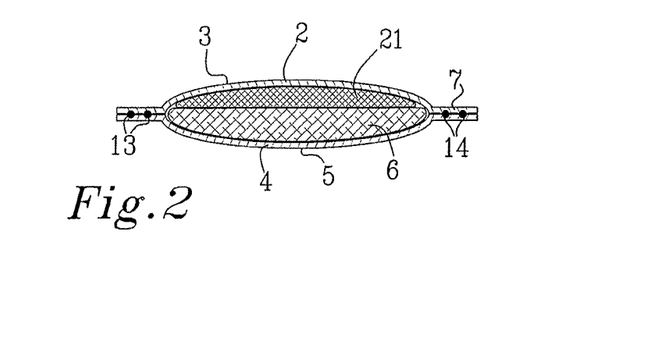
FIG. 2 shows a cross-section through the incontinence protector in FIG. 1, taken along the line II-II.

A separate topsheet layer as shown in FIGS. 1 and 2 is optional to the incontinence protectors. The incontinence protector may be provided with an absorbent core having high coherence and wear resistance so that no separate topsheet component is needed. On the other hand, if the amount of urine that the incontinence protector is expected to receive is very small, a topsheet material may provide sufficient absorption capacity, so that it may be possible to dispense with a separate absorbent core component.

In particular embodiments, the backsheet 4 is liquid impermeable. However, backsheet materials that are only resistant to liquid penetration may be used particularly in instances where only small amounts of urine are expected to be taken up by the incontinence protector. The backsheet 4 is commonly constituted by a thin, flexible, liquid-impermeable plastic film, but liquid-impermeable nonwoven materials, liquid impermeable foams and liquid impermeable laminates are also known in the art. The backsheet 4 may be breathable, implying that air and vapor may pass through the backsheet. Another type of backsheet that is common in the art has an outer, garment-facing surface of a textile material such as nonwoven.

The absorbent core 6 may be made up of any suitable absorbent or fluid uptake material as known in the art, such as one or more layers of cellulose fluff pulp, foam, fibre waddings, etc. The absorbent core 6 may contain fibers or particles of highly absorbent polymer material, commonly known as superabsorbents, which are materials having the ability to absorb and retain large quantities of liquid upon formation of a hydrogel. The superabsorbents may be mixed with cellulose fluff pulp and/or may be arranged in pockets or layers in the absorbent core 6. The absorbent core 6 may further incorporate components for improving the properties of the absorbent core 6. Some examples of such components are binder fibers, liquid-dispersing materials, wetness indicators, liquid acquisition materials, etc. as known in the art.

The incontinence protector 1 as shown in FIGS. 1-4 has an essentially isosceles triangular shape or essentially isosceles trapezoid shape when fully extended in all directions. The word "essentially" in this context means that, for instance, the corners of the incontinence protector 1 may be rounded, or that the edges of the incontinence protector 1 may not be completely linear, but that the incontinence protector 1 has the general shape described herein. The incontinence protector 1 has two inclined longitudinal side edges 8, 9 having equal length and extending generally in the same direction as a longitudinal center line 10 through the incontinence protector 1. A third edge constitutes the front end edge 11 of the incontinence protector 1 and extends transversely to the longitudinal center line 10 of the incontinence protector 1. The incontinence protector 1 further has a rear end edge 12, also extending generally transversely to the longitudinal center line 10 of the incontinence protector 1. The rear end edge 12 is intended to be orientated rearwards during use of the incontinence protector 1, and the front end edge 11 is intended to be facing forwards towards the abdomen of the wearer.

The incontinence protector 1 is shown having pre-stretched elongate elastic elements 13, 14 extending along each side edge 8, 9 in the edge join 7 outside the absorbent core 6. Such elastic elements 13, 14 are optional and may be omitted, if desired. The elastic elements 13, 14 may, for instance, be in the form of elastic threads, bands or the like. The use of elastic foam material is also conceivable. The elastic elements 13, 14 are preferably adhesively attached to one or to both of the topsheet or backsheet 2, 4. The elastic elements 13, 14 urge the incontinence protector 1 into a basin-like shape cupping the genitals of the wearer and helping to maintain a close fit between the incontinence protector 1 and the wearer's body.

The incontinence protector 1 is divided along its transverse centre line 15 into a front end portion 16 and a rear end portion 17 as shown in FIG. 1. The rear end portion 17 is the part of the incontinence protector 1 that is intended to be placed in a wearer's groin and to extend between and preferably rearward of the space limiting tendons in the groin when the incontinence protector 1 is being worn.

In the embodiment shown in FIG. 1, adhesive fastening means 18 are arranged on the garment-facing surface 5 in the front end portion 16, near the front end edge 11. The fastening means 18 are merely supplemental fastening means and may be omitted, if desired. In FIG. 1, the fastening means 18 are shown to be in the form of a row of rectangular adhesive areas. However, any other suitable adhesive pattern may be used such as a continuous adhesive string or band, one or more circular dots, etc. The adhesive may be any pressure sensitive adhesive as conventionally used for the purpose. In order to protect the adhesive fastening means 18 against contamination or unwanted attachment prior to use, the fastening means may be covered by a releasably attached protective strip 19. Other types of fastener elements may be contemplated such as hook-and-loop fasteners, other mechanical fastening means or combinations of mechanical and adhesive fasteners, as known in the art. In particular embodiments, the supplemental fastening means 18 is arranged in the front end portion, so as to interfere as little as possible with the body-contacting fastening of the rear end portion 17.

Furthermore, body-fastening adhesive may be used to enhance the effect of the tendon engagement means. In certain embodiments, the body adhesive is arranged on the body contacting surface in the rear end portion 17 of the incontinence protector 1. Body adhesive may also be arranged at the edges of the incontinence protector.

In accordance with embodiments of the invention, tendon engagement means 20 in the form of a tendon abutment element 21 is arranged in the rear end portion 17.

The tendon abutment element 21 is a stiffening component and is shown in FIG. 1 as a circular disc of material placed at the edge of the absorbent core 6 at the rear end edge 12 of the incontinence protector 1. The tendon abutment element 21 may have a diameter, d, of from 40 mm to 70 mm, preferably of from 45 mm to 60 mm.

The tendon abutment element 21 may be made from an absorbent material or a non-absorbent material, as desired. If made from an absorbent material it will aid in absorbing and retaining any liquid running rearward in the incontinence protector 1. The absorbent tendon abutment element 21 may contain superabsorbents in order to increase the absorbent capacity of the rear end portion 17 and to immobilise any liquid absorbed by the tendon abutment element 21. Alternatively, the tendon abutment element 21 may be made from a non-absorbent material that will serve as a barrier against rearward liquid flow.

The tendon abutment element 21 is shown in FIG. 2 to be placed between the topsheet 2 and the absorbent core 6. However, other contemplated locations for the tendon abutment element 21 are on the wearer-facing surface 3 of the topsheet 2, between layers in the topsheet 2, inside the absorbent core 6, on the outside or garment-facing surface 5 of the backsheet 4, or between layers in the backsheet 4.

The material in the tendon abutment element 21 is selected such that it will significantly increase the resistance to lateral deformation such as bending and lateral compression within the area of the tendon abutment element 21 as compared to the material in remaining parts of the rear end portion 12.

Figure 3:
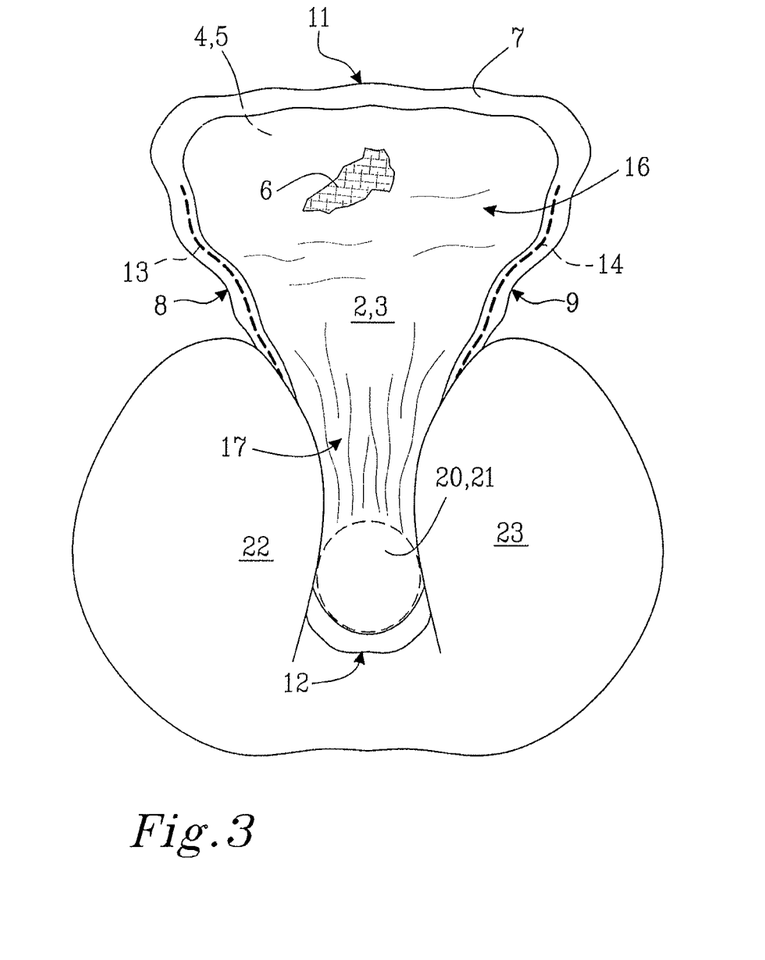
FIG. 3 shows the incontinence protector in FIGS. 1 and 2 when worn and seen from the side which is facing the wearer.
Figure 4:
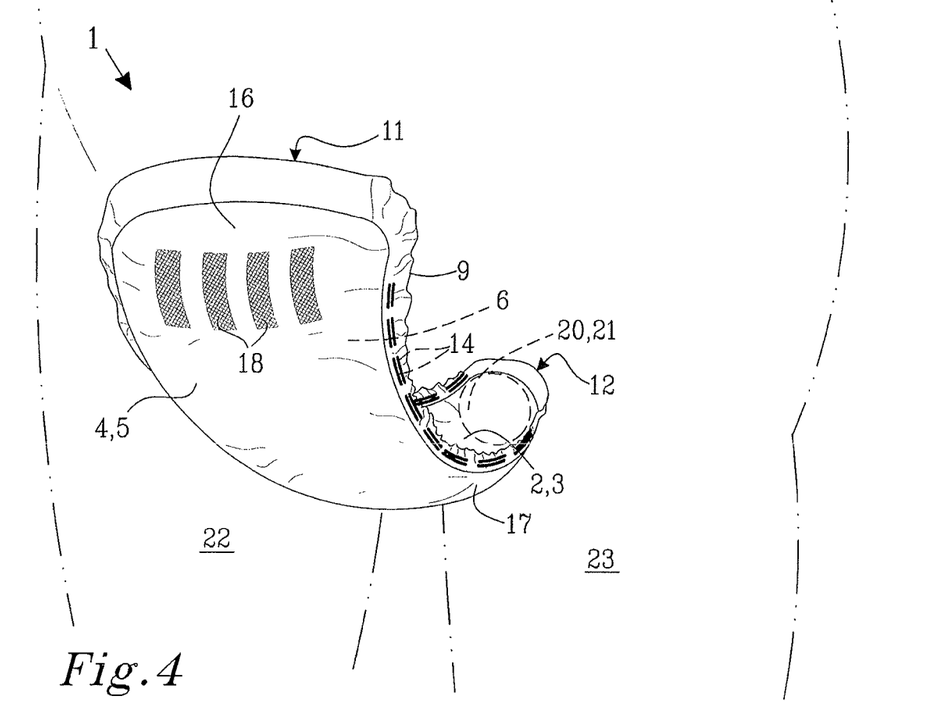
FIG. 4 shows a perspective view of the incontinence protector in FIGS. 1-3 when worn.

When the incontinence protector 1 is being worn, it is positioned in the wearer's groin, as shown in FIGS. 3 and 4 with the rear end portion 17 placed between the wearer's thighs 22, 23 and the front end portion 16 extending up towards the wearer's abdomen.

In the embodiment shown in FIGS. 1-4, the tendon abutment element 21 is placed at the very end of the absorbent core 6, implying that the tendon engagement means 20 is arranged in the incontinence protector 1 at a distance from the rear end edge 12 corresponding to the width of the edge join 7 outside the absorbent core 6 and extends in the rear end portion 17 up to a distance from the rear end edge 12 corresponding to the width of the edge join 7 and the diameter, d of the tendon abutment element 21.

During use of the incontinence protector 1, the tendon abutment element 21 will be placed rearward of the wearer's genitalia and will be fitted between the wearer's thighs 22, 23, as shown in FIG. 3. Accordingly, when correctly positioned in the wearer's groin, the tendon abutment element 21 will be in abutting contact with the insides of the wearer's thighs 22, 23 in the narrow area between the tendons of the muscle groups which extend from the inside of the base of the pelvis down along each thigh and with the widest portion of the tendon abutment element 21 positioned slightly behind the narrowest part of the groin. By selecting the width or maximum transverse extension of the tendon abutment element 21 such that it along at least part of the extension of the tendon abutment element 21 in the longitudinal direction of the incontinence protector 1 is somewhat larger than the distance between the tendons of the muscle groups, it is ascertained that the tendon abutment element 21 will always be able to hook against the tendons ensuring that the incontinence protector 1 will be held firmly and securely in the correct position against the body of the wearer. As is shown in FIG. 3, the rear end portion 17 of the incontinence protector 1 is slightly squeezed between the thighs 22, 23 of the wearer in the part of the rear end portion 17 being located forward of the tendon abutment element 21. This squeezing action contributes to keep the incontinence protector 1 clamped between the thighs 22, 23 while the tendon abutment element 21 gives rise to a hooking effect against the space-limiting tendons on the insides of the thighs, thus preventing the incontinence protector 1 from moving in the longitudinal direction.

The body-conforming fastening offered by the tendon abutment element 21 would normally be sufficient in order to keep the incontinence protector 1 in the correct position against the body of the wearer. The tendon abutment element 21 counteracts unwanted displacement of the incontinence protector 1 that may ultimately result in the incontinence protector 1 being moved into a position where it will fail to absorb and retain all excreted urine, causing the incontinence protector 1 to leak. At the same time, when used alone, without any supplemental fastening element 18, the body-conforming fastening according to the invention allows the front portion 16 of the incontinence protector 1 to shift slightly in relation to the body of the wearer, thus adding to wearer comfort.

Figure 5A:
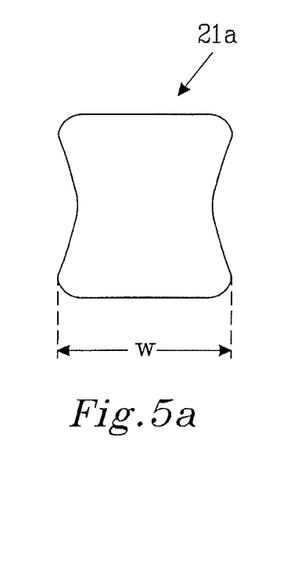
Figure 5B:
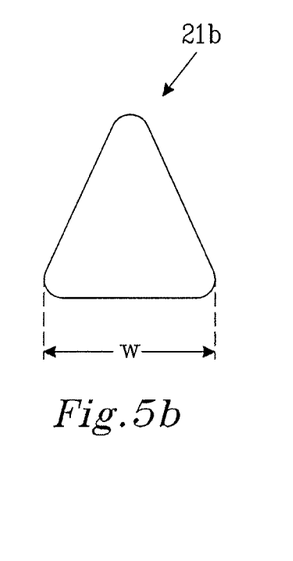
Figure 5C:
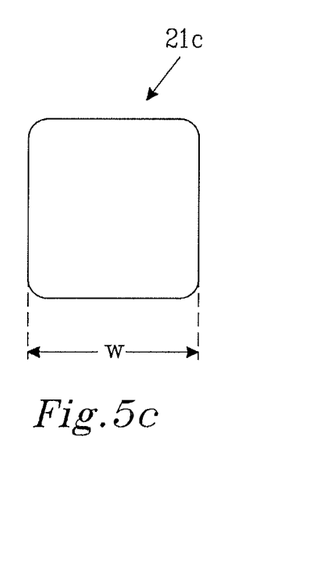

FIGS. 5*a-c* show tendon abutment elements 21*a*, 21*b*, 21*c* of alternative shapes. In particular embodiments, the tendon abutment elements 21*a*, 21*b*, 21*c* have a maximum extension, w, in the transverse direction of from 40 mm to 70 mm, preferably from 45 mm to 60 mm. The tendon abutment elements 5*a*, 5*b* also have a minimum extension in the transverse direction that is less than the maximum extension.

Figure 6:
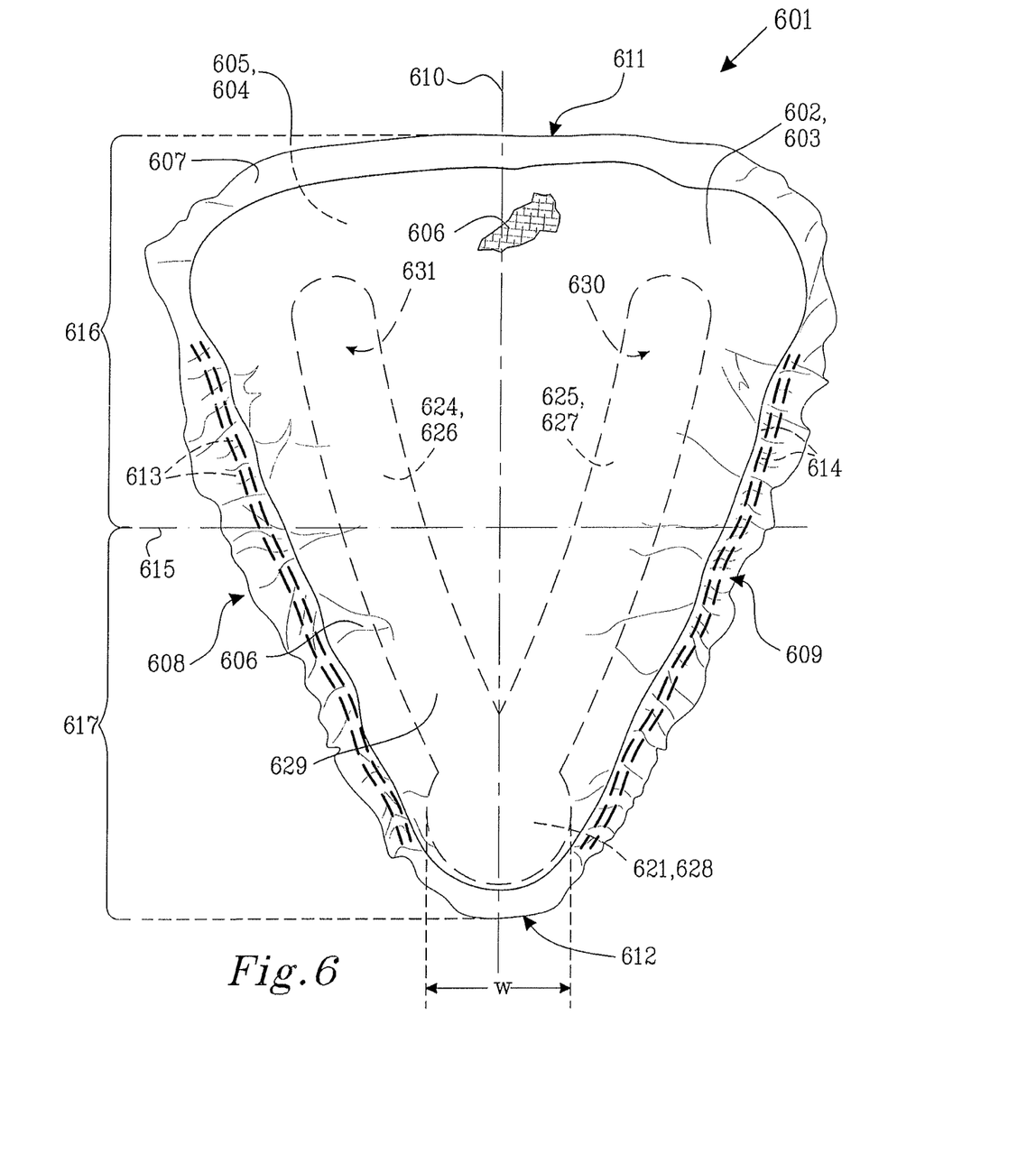
FIG. 6 shows an incontinence protector according to an embodiment of the invention, seen from the side which will be facing the wearer when the incontinence protector is being worn.

The incontinence protector 601 shown in FIG. 6 is viewed from the side of the incontinence protector 601 that will be facing the wearer when the incontinence protector 601 is being worn. The incontinence protector 601 has the same general configuration and composition as the incontinence protector 601 shown in FIGS. 1-4. Accordingly, the incontinence protector 601 includes a liquid-permeable topsheet 602, disposed at the wearer-facing surface 603 of the incontinence protector 601, a backsheet 604 disposed at the garment-facing surface 605 of the incontinence protector 601, and an absorbent core 606, enclosed between the topsheet 602 and the backsheet 604.

The topsheet 602 and the backsheet 604 extend together laterally outside of the absorbent core 606 along the whole circumference of the absorbent core 606 and are connected to each other in an edge join 607 outside the absorbent core 606.

The incontinence protector 601 has two inclined longitudinal side edges 608, 609 having equal length and extending generally in the same direction as a longitudinal center line 610 through the incontinence protector 601. A front end edge 611 of the incontinence protector 601 extends generally parallel to the transverse centre line 615, transversely to the longitudinal center line 610 of the incontinence protector 601. The incontinence protector 601 further has a rear end edge 612, also extending generally transversely to the longitudinal center line 610 of the incontinence protector 601.

The incontinence protector 601 differs from the incontinence protector 1 shown in FIGS. 1-4 in that side edge shaping means 624, 625 in the form of absorbent or non-absorbent elongate shaping elements 626, 627 are arranged along the side edges 608, 609 of the incontinence protector 601. The tendon abutment element 621 and the elongate shaping elements 626, 627 are formed as integrated parts of a coherent insert 629 where a base portion 628 placed in the rear end portion 617 of the incontinence protector 601 constitutes the tendon abutment element 621 and two diverging leg portions 630, 631 extending from the base portion 628 forward along the side edges 608, 609 of the incontinence protector 601 constitute the side edge shaping means 624, 625.

When the incontinence protector 601 is worn, the side edge shaping means 624, 625 serve to enhance the anatomical fit of the incontinence protector 601 by creating a cup-shape in the incontinence protector 601, at least in the transverse direction and optionally also in the longitudinal direction of the incontinence protector 601.

In certain embodiments, the maximum width, w, of the base portion 628 of the insert 629 is from 40 mm to 70 mm, preferably from 45 mm to 60 mm in order to achieve an optimal hooking effect between the tendons in the wearer's groin.

Figure 7:
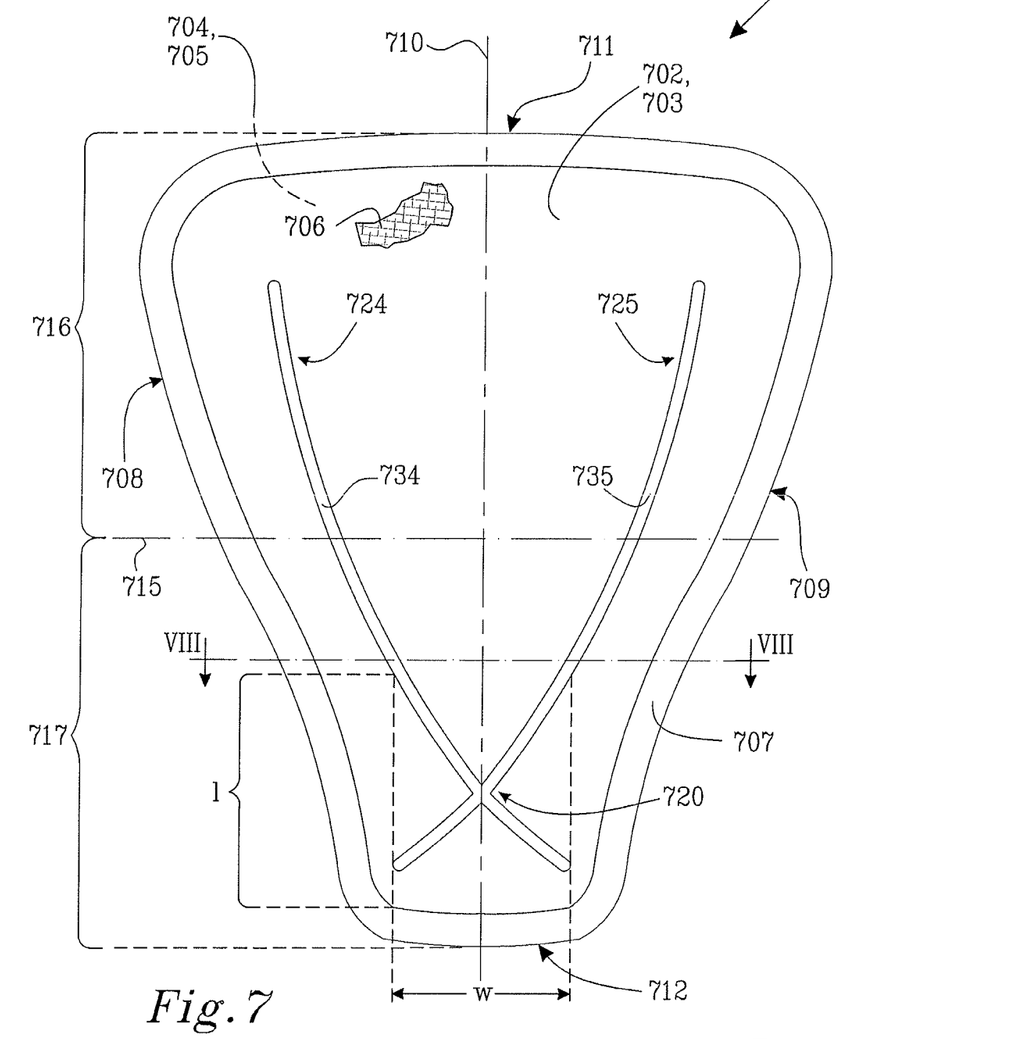
FIG. 7 shows an incontinence protector according to an embodiment of the invention, seen from the side which will be facing the wearer when the incontinence protector is being worn.
Figure 8:
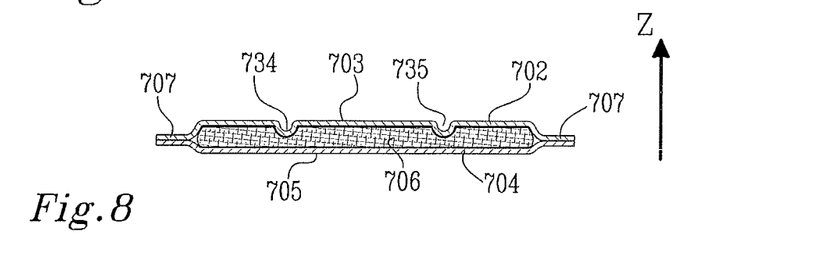
FIG. 8 shows a cross-section through the incontinence protector in FIG. 7, taken along the line VIII-VIII.

FIGS. 7 and 8 show an incontinence protector 701 according to a further embodiment of the invention. The incontinence protector 701 is shown from that side of the incontinence protector 701 that will be facing the wearer when the incontinence protector 701 is being worn. The incontinence protector 701 has the same general configuration and composition as the incontinence protectors 1, 601 shown in FIGS. 1-4 and 6. Accordingly, the incontinence protector 701 includes a liquid-permeable topsheet 702, disposed at the wearer-facing surface 703 of the incontinence protector 701, a backsheet 704 disposed at the garment-facing surface 705 of the incontinence protector 701, and an absorbent core 706, enclosed between the topsheet 702 and the backsheet 704.

The topsheet 702 and the backsheet 704 extend together laterally outside of the absorbent core 706 along the whole circumference of the absorbent core 706 and are connected to each other in an edge join 707 outside the absorbent core 706.

The incontinence protector 701 has two inclined longitudinal side edges 708, 709 having equal length and extending generally in the same direction as a longitudinal center line 710 through the incontinence protector 701. A front end edge 711 of the incontinence protector 701 extends generally parallel to the transverse centre line 715, and transversely to the longitudinal center line 710 of the incontinence protector 701. The incontinence protector 701 further has a rear end edge 712, also extending generally transversely to the longitudinal center line 710 of the incontinence protector 701.

The incontinence protector 701 differs from the incontinence protectors 1, 601 shown in FIGS. 1-4 and 6 in that it does not have elastic elements along the side edges. However, such elastic elements may be added if desired.

Moreover, the incontinence protector 701 includes tendon engagement means 720 and side edge shaping means 724, 725 formed by two elongated grooves 734, 735. Each groove 734, 735 has a first portion extending along a side edge 708, 709 from the front end portion 716 into the rear end portion 717 and constituting a side edge shaping means 724, 725 and a second portion extending only in the rear end portion 717 and forming one part of the tendon engagement means 720. The second portions of the elongated grooves 734, 735 intersect in the rear end portion 717 of the incontinence protector 717 to form a tendon engagement means 720 having an X-configuration. The tendon engagement means 720 has a maximum width, w, and a length, f. In the embodiment shown in FIGS. 7 and 8, the maximum width, w is equal to the length, t. However, embodiments where w is greater than t or w is smaller than f are also conceivable. In particular embodiments, the maximum width, w, of the tendon engagement means 720 is from 40 mm to 70 mm, preferably from 45 mm to 60 mm. In certain embodiments, the length, t, of the tendon engagement means 720 is up to 30 mm, preferably from 5 to 30 mm.

The grooves may have been formed by embossing from the wearer-facing surface 703 of the incontinence protector 701 so that the topsheet 702 and at least a part of the absorbent core 706 in the thickness direction, Z, have been compacted within the area of the groove 734, 735 as shown in FIG. 8. In particular embodiments, the embossing is heat embossing at a temperature where any thermoplastic material in the topsheet 702 and in the absorbent core 706 will melt or at least soften to promote binding of the material in the grooves, thereby providing enhanced stability of the elongated grooves 734, 735. The compaction of the material in the grooves 734, 735 and any additional thermobonding of the material in the grooves 734, 735 increase stiffness and bending resistance in the grooves 734, 735.

When the incontinence protector 701 is worn, it is placed with the rear end portion 717 between the wearer's legs in the manner shown in FIG. 3. Accordingly, during wearing of the incontinence protector 701, the X-shaped tendon engagement means 720 will be located in the wearer's groin between the space-limiting tendons on each side of the groin. The incontinence protector 701 will automatically adjust itself to fit with the narrow center portion of the X between the tendons in the narrowest part of the groin. The stiffened forward and rearward arms of the X will abut the tendons in a hooking manner, thus counteracting forward and rearward movement of the incontinence protector 701.

The portions of the grooves 734, 735 located along the side edges 708, 709 forward of the tendon engagement means 720 form side edge shaping means 724, 725 responding to pressure in the width direction of the incontinence protector 701 by inducing bending of the incontinence protector 701 along the grooves 734, 735 to create a cup-shape over the genitalia of the wearer. The parts of the grooves 734, 735 forming the side edge shaping means 724, 725 will also act as side leakage barriers by restricting fluid flow across the grooves 734, 735 and promoting liquid flow along the grooves 734, 735.

In certain embodiments, the parts of the grooves 734, 735 that form side edge shaping means 724, 725 are placed at a distance from the side edges 708, 709 of from 10 mm to 30 mm. Further grooves may be arranged along the first set of grooves 734, 735, between the side edges 708, 709 and the first set of grooves 734, 735 and/or between the longitudinal centre line 710 and the first set of grooves 734, 735 to further enhance shaping of the forward part of the incontinence protector 701 around the wearer's genitalia. The elongated grooves 734, 735 may also be supplemented by further side edge shaping means in the form of elongate elements as described in connection with the embodiment shown in FIG. 6.

The grooves 734, 735 may have a width of from 1 mm to 20 mm and a depth of from 1 mm to 20 mm measured at zero load.

The grooves 734, 735 may have uniform width and depth over their full length or may vary in width and/or depth along their length. If additional grooves are arranged as side edge shaping means, these additional grooves may have widths and depths differing from those of the first set of grooves 734, 735 shown in FIG. 7. The side edge shaping grooves 734, 735 need not be compressed grooves but can be grooves formed by removing material from the absorbent core. Such grooves will not be stiffer than surrounding parts of the absorbent core. However, the grooves will act as liquid transporting channels and as hinge means for bending the side edges into a cup-shape.

Figure 9:
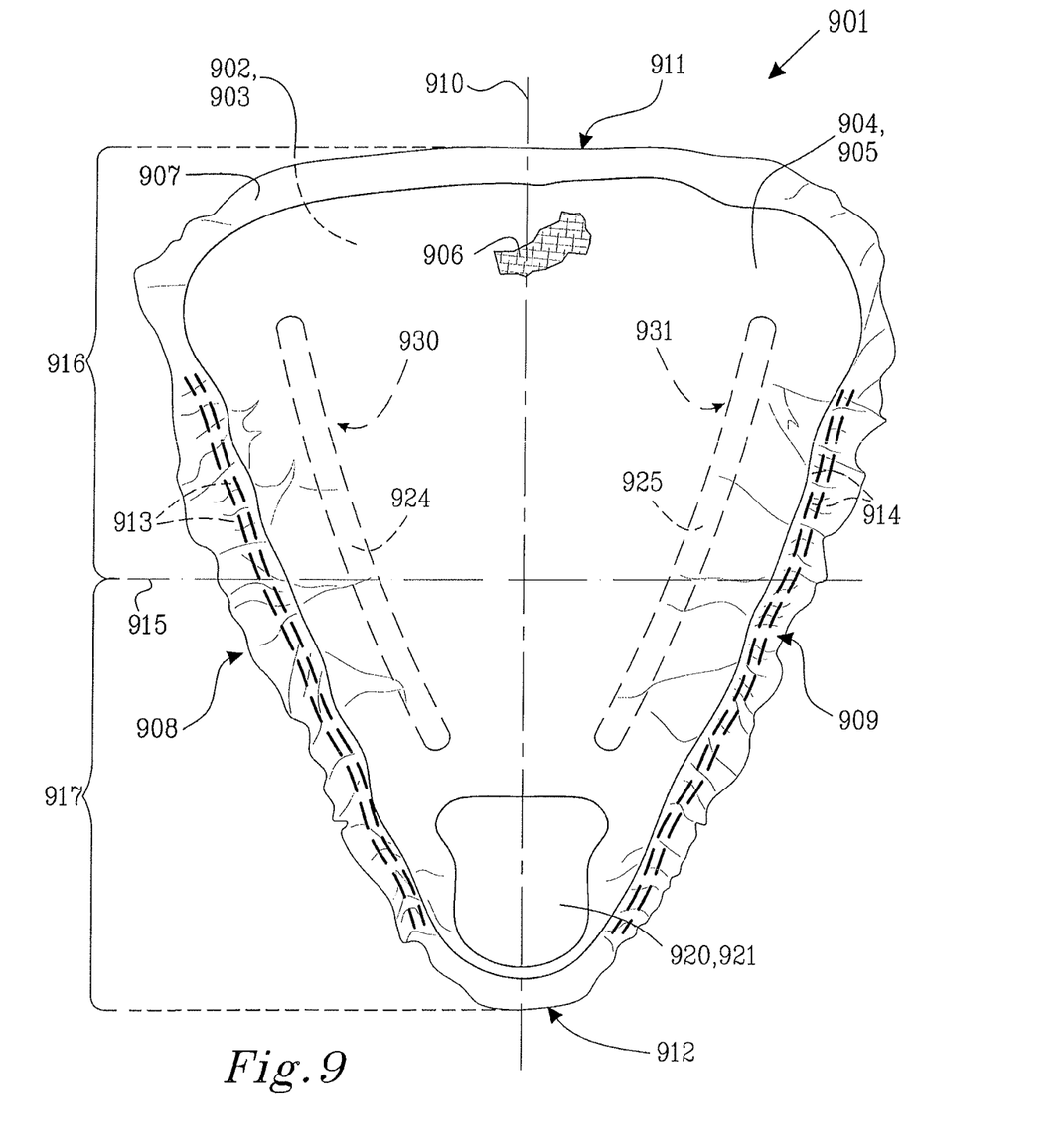
FIG. 9 shows an incontinence protector according to an embodiment of the invention, seen from the side which will be facing the undergarment when the incontinence protector is being worn.

The incontinence protector 901 shown in FIG. 9 is shown from the side 905 of the incontinence protector 901 that will be facing the undergarment when the incontinence protector 901 is being worn. The incontinence protector 901 has the same general configuration and composition as the incontinence protector 601 shown in FIG. 6. Accordingly, the incontinence protector 901 includes a liquid-permeable topsheet 902, disposed at the wearer-facing surface 903 of the incontinence protector 901, a backsheet 904 disposed at the garment-facing surface 905 of the incontinence protector 901, and an absorbent core 906, enclosed between the topsheet 902 and the backsheet 904.

The topsheet 902 and the backsheet 904 extend together laterally outside of the absorbent core 906 along the whole circumference of the absorbent core 906 and are connected to each other in an edge join 907 outside the absorbent core 906.

The incontinence protector 901 has two inclined longitudinal side edges 908, 909 having equal length and extending generally in the same direction as the longitudinal center line 910 through the incontinence protector 901. A front end edge 911 of the incontinence protector 901 extends generally parallel to the transverse centre line 915, and perpendicular to the longitudinal center line 910 of the incontinence protector 901. The incontinence protector 901 further has a rear end edge 912, also extending generally perpendicular to the longitudinal center line 910 of the incontinence protector 901.

Pre-stretched elastic elements 913, 914 are arranged along the side edges 908, 909 to form the incontinence protector 901 into a curve shape.

The incontinence protector 901 differs from the incontinence protector 601 shown in FIG. 6 in that side edge shaping means 924, 925 in the form of absorbent or non-absorbent elongate shaping elements 926, 927 are arranged as separate elements along the side edges 908, 909 of the incontinence protector 901. The elongate shaping elements 926, 927 are placed between the topsheet 902 and the backsheet 904. The tendon engagement means 920 is in the form of a separate tendon abutment element 921 that is placed on the outside or garment-facing side 905 of the backsheet 904. The tendon abutment element 921 may be a reinforcement material such as a relatively rigid nonwoven material, plastic layer, foam layer, etc. The tendon abutment element may have fastening properties in addition to the tendon engagement function and may consist of or comprise a fastener element such as one part of a hook-and-loop arrangement, a friction increasing layer or an adhesive fastener.

The FIG. 9 embodiment illustrates the possibility of having the tendon engagement means 920 and the side edge shaping means 924, 925 made as separate elements that may be placed on the backsheet, the topsheet or between the backsheet and the topsheet as desired and independently of each other.

Figure 10:
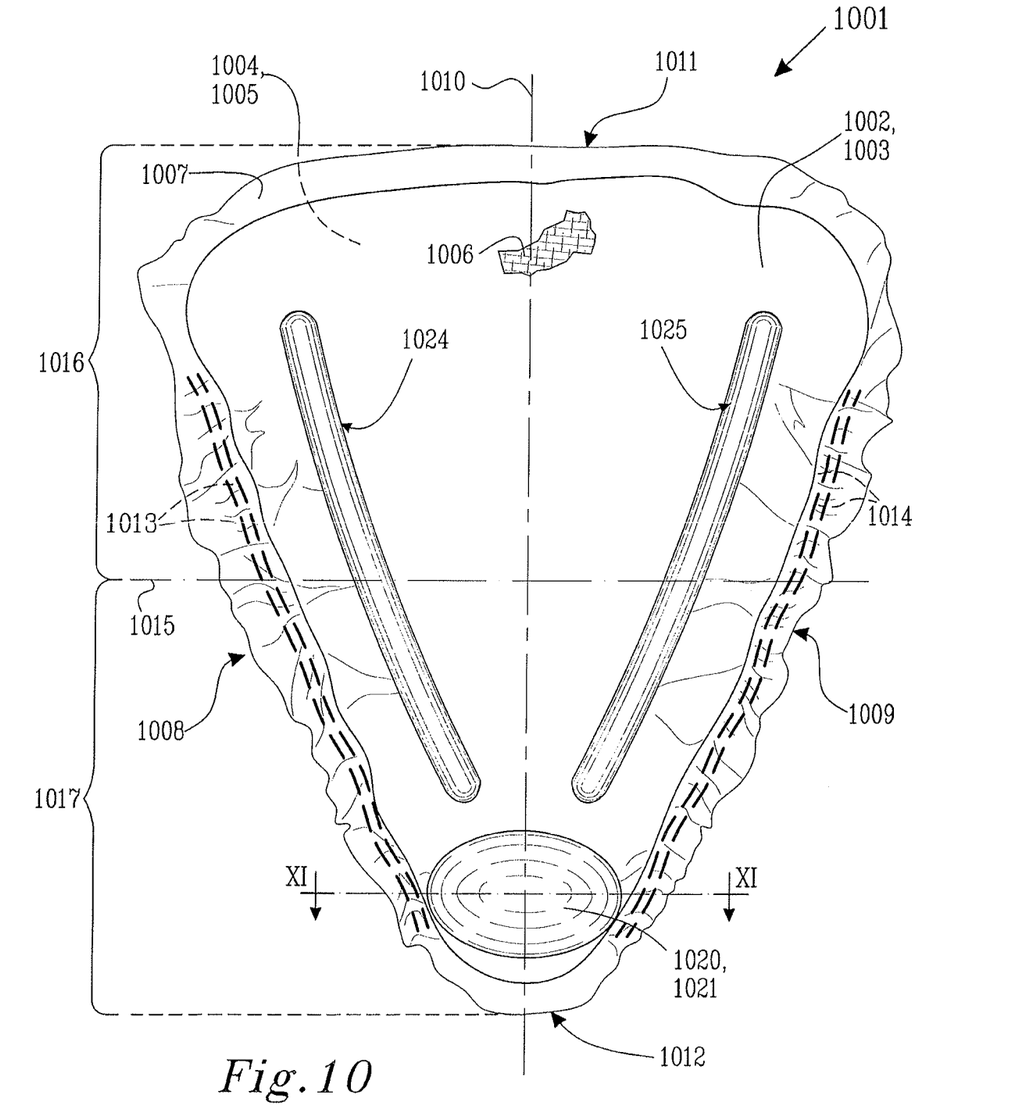
FIG. 10 shows an incontinence protector according to an embodiment of the invention, seen from the side which will be facing the wearer when the incontinence protector is being worn.

FIG. 10 shows an incontinence protector 1001, seen from the side 1003 which will be facing the wearer when the incontinence protector is being worn. The incontinence protector 1001 has the same general configuration and composition as the incontinence protector 901 shown in FIG. 9. Accordingly, the incontinence protector 1001 includes a liquid-permeable topsheet 1002 disposed at the wearer-facing surface 1003 of the incontinence protector 1001, a backsheet 1004 disposed at the garment-facing surface 1005 of the incontinence protector 1001, and an absorbent core 1006, enclosed between the topsheet 1002 and the backsheet 1004.

The topsheet 1002 and the backsheet 1004 extend together laterally outside of the absorbent core 1006 along the whole circumference of the absorbent core 1006 and are connected to each other in an edge join 1007 outside the absorbent core 1006.

The incontinence protector 1001 has two inclined longitudinal side edges 1008, 1009 extending generally in the same direction as the longitudinal center line 1010 through the incontinence protector 1001. A front end edge 1011 of the incontinence protector 1001 extends generally parallel to the transverse centre line 1015. The incontinence protector 1001 further has a rear end edge 1012, also extending generally transversely to the longitudinal center line 1010 of the incontinence protector 1001.

Pre-stretched elastic elements 1013, 1014 are arranged along the side edges 1008, 1009 to form the incontinence protector 1001 into a curve shape.

The incontinence protector 1001 differs from the incontinence protector 901 shown in FIG. 9 in that side edge shaping means 1024, 1025 are arranged on the wearer-facing surface 1003 of the topsheet 1002 in the form of absorbent or non-absorbent elongate raised shaping elements. A "raised" element as defined herein is an element that may be identified by the naked eye as protruding from a surrounding surface. Accordingly, the elongate raised shaping elements in FIG. 10 will be seen as being raised from the surrounding portions of the wearer-facing surface 1003.

Figure 11:
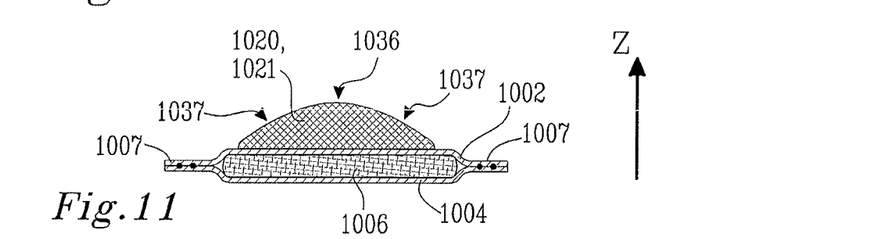
FIG. 11 shows a cross-section through the incontinence protector in FIG. 10, taken along the line XI-XI.

The tendon engagement means 1020 is in the form of a separate tendon abutment element 1021 that is placed on the outside or wearer-facing side 1003 of the topsheet 1002. As seen in the cross-section in FIG. 11, the tendon abutment element 1021 is a three-dimensional hump that is raised from the wearer-facing surface 1003 of the topsheet 1002. The hump is shown in FIG. 11 with oval circumference and having a central peak 1036 with sloping sides 1037. The hump shaped tendon abutment element 1021 has the dual functions of constituting a retaining element for keeping the incontinence protector 1001 securely held in position against the body of a wearer of the incontinence protector 1001 and of providing a gasket seal against rearward leakage of urine.

In a particular embodiment, the tendon abutment element 1021 is made of a material that is resiliently compressible in the Z-direction or thickness direction such that it will at least to some degree regain its uncompressed extension in the Z-direction after having been subjected to a Z-direction compressive force such as arising under normal wearing conditions such as when the wearer is sitting down. In certain embodiments, the tendon abutment element 1021 is resilient both under wet and dry conditions. A Z-direction resilient tendon abutment element 1021 will constantly change its height as the wearer moves, sits down or stands up so that the seal provided by the close contact between the tendon abutment element 1021 and the wearer will be maintained throughout the wearing period.

The hump may be formed from a wad of fibres, for example, comprising a major proportion of hydrophobic resilient polymer fibres such as crimped fibres of polypropylene, polyethylene, polyester or multicomponent fibres. Other suitable materials are rolled non-woven sheets or shaped foam bodies. The hump may be constructed from one or more layers or parts with different properties, such as different compositions, different thickness, different density, different area, different bending resistance, etc. The hump may include superabsorbent material. The tendon abutment element 1021 function may be provided by a special layer or element in the hump. Although the hump is shown as being placed on the outside of the topsheet 1002, it should be understood that the hump may alternatively be placed on the inner side of the topsheet 1002.

The tendon abutment element 1021 may be substantially non-compressible in the transverse direction of the incontinence protector 1001. The tendon abutment element 1021 may be very stiff and may have very high bending resistance such as a layer of cardboard paper, a metal insert, a hard plastic insert, or similar. In a particular embodiment, the maximum transverse extension of the tendon abutment element 1021 exceeds the transverse extension of the narrow area in the wearer's groin. Accordingly, in a particular embodiment, the maximum transverse extension of the tendon abutment element 1021 is from 40 mm to 70 mm, preferably from 45 mm to 60 mm.

In the embodiment shown in FIGS. 10 and 11, the hump in the rear end portion of the incontinence protector is both a tendon abutment element and a gasket element. However, it is conceivable to separate these functions so that the hump is made of a material that is soft and conformable in the lateral direction to such a degree that is has no practical effect as a tendon engagement means. In such embodiments, a separate tendon engagement means such as a tendon abutment element or one or more elongate grooves or compressed areas as disclosed herein will be arranged in the rear end portion of the incontinence protector in addition to the hump. A separate tendon engagement means need not be placed in direct contact with the gasket hump, but may be placed anywhere in the Z-direction of the incontinence protector and even out of longitudinal register with the gasket hump.

FIGS. 12a-f illustrate alternative forms of the tendon engagement means and side edge shaping means. FIGS. 12a-f also show some of the possible combinations of tendon engagement means and side edge shaping means conceivable within embodiments of the invention.

Figure 12A:
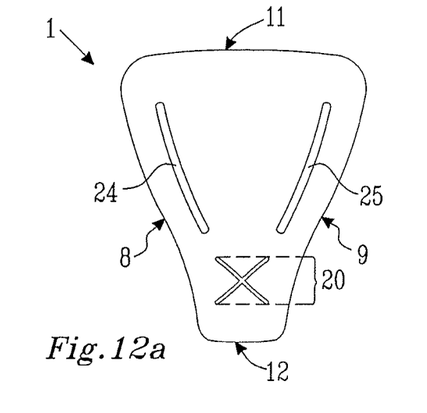
FIGS. 12a-12f show examples of different designs and combinations of tendon engagement means and side edge shaping means according to embodiments of the invention.

FIG. 12a shows tendon engagement means 20 in the form of elongated grooves arranged in the form of an X and side edge shaping means 24, 25 arranged as elongate elements along the side edges 8, 9 of the incontinence protector 1.

Figure 12B:
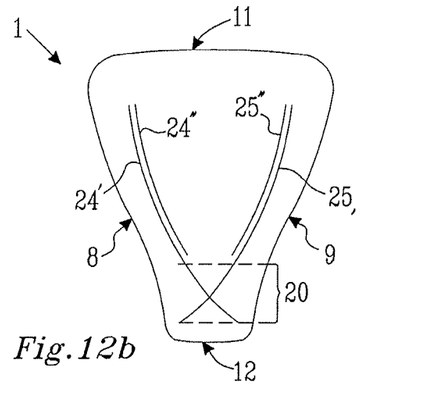

FIG. 12*b* shows tendon engagement means 20 in the form of elongated grooves arranged in the form of the letter X and being continuous with side edge shaping means arranged as elongated grooves 24', 25' along the side edges 8, 9 of the incontinence protector 1. Furthermore, the side edge shaping means in FIG. 12*b* include supplemental grooves 24", 25" arranged laterally inside of the first grooves 24', 24'.

Figure 12C:
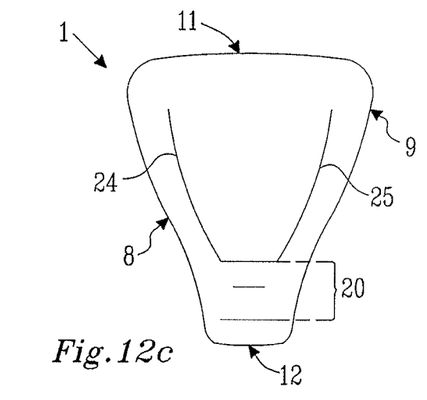

FIG. 12*c* shows tendon engagement means 20 in the form of three elongated grooves arranged in the transverse direction of the incontinence protector 1 in the form of the Greek letter Ξ and side edge shaping means 24, 25 arranged as elongate grooves along the side edges 8, 9 of the incontinence protector 1.

Figure 12D:
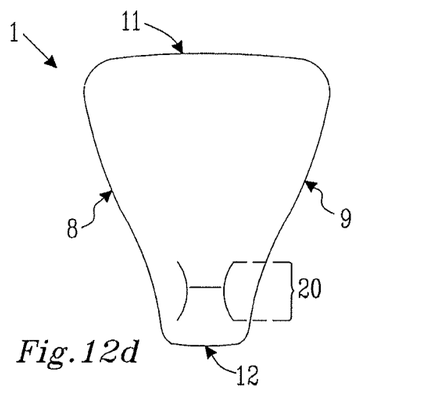

FIG. 12*d* shows an incontinence protector 1 without side edge shaping means and having tendon engagement means 20 in the form of three elongated grooves arranged in the shape of the letter H with slightly curved legs.

Figure 12E:
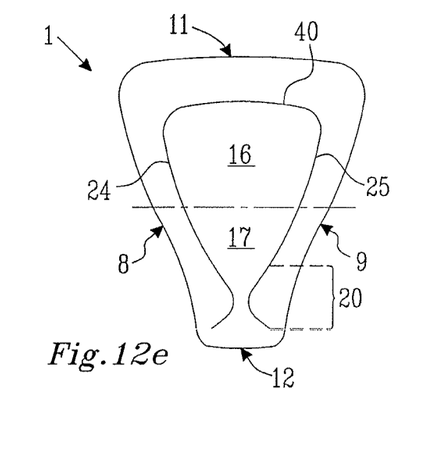

FIG. 12*e* shows an incontinence protector 1 having elongated grooves arranged continuously from near the front end edge 11 along the side edges 8, 9 in the front end portion 16 of the incontinence protector 1 and into the rear end portion 17 to terminate near the rear end edge 12 of the incontinence protector 1. The elongated grooves run together in the rear end portion 17 and form an hour-glass shape with a constricted waist portion. The elongated grooves constitute both side edge shaping means 24, 25 and tendon engagement means 20.

A transverse shaping means 40 is arranged in the front end portion 16 of the incontinence protector 1, along the front end edge 11 of the incontinence protector. The transverse shaping means 40 is arranged between the side edge shaping means 24, 25 and is shown in FIG. 12*e* as being continuous with the side edge shaping means 24, 25.

Alternatively, a transverse shaping means may be arranged separately from the side edge shaping means or may be arranged in an incontinence protector without side edge shaping means such as that shown in FIG. 12*d*. The transverse shaping means 40 is a stiffened structure that keeps the front end edge stretched out when the incontinence protector is worn and contributes to the formation of a cup-shape by being a transverse hinge in the front end portion of the incontinence protector. The transverse shaping means 40 will also be a barrier to longitudinal liquid flow across the transverse shaping means 40 as all grooves and channels in an absorbent article tend to promote liquid flow in the length direction of the groove and inhibit liquid flow in the width direction of the groove.

As an alternative to creating grooves as shaping means and tendon engagement means, such as those shown in FIG. 12*e*, the whole or part of the area within the contour of the groove in FIG. 12*e* may have higher resistance to bending and lateral compression than the surrounding edge portions of the incontinence protector. In this manner, the edges of the stiffer central area of the incontinence protector will act as hinges about which the edge portions may bend to create a cup-shape over a wearer's genitals when the incontinence protector is worn between the wearer's legs. An area with higher resistance to bending and lateral compression than surrounding portions of the incontinence protector may be formed by compression, by increasing the amount of material in the more rigid area, by using reinforcing/stiffening components, by selective bonding, or by combinations of two or more of these measures.

Figure 12F:
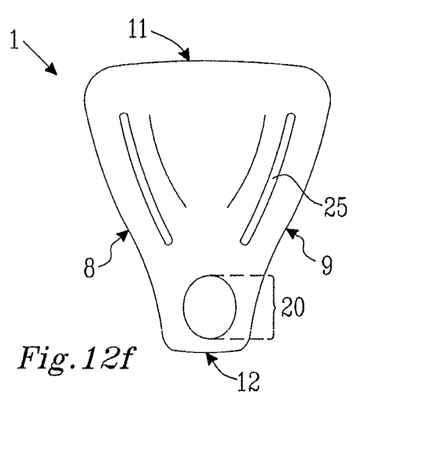

FIG. 12*f* shows tendon engagement means 20 in the form of a tendon abutment element and side edge shaping means including elongate elements 24', 25' arranged along the side edges 8, 9 of the incontinence protector 1 and supplemental slightly curved grooves 24", 25" arranged laterally inside of the elongate elements 24', 24'.

The embodiments shown in FIGS. 12*a-f* constitute only some examples of possible combinations and designs for the tendon engagement means and side edge shaping means and it is to be understood that further combinations and variations are conceivable. Further examples of suitable shapes of grooves forming the tendon engagement means are Y, V, inverted Y and V, opposing arrows ><, one or more horizontal groove—, etc.

The tendon engagement means may be formed by creating cut-out portions at the side edges of an absorbent core or layer or in a non-absorbent insert. The cut-outs will constitute portions of the incontinence protector having reduced stiffness as compared to portions forward and rearward of the cut-out portions. In certain embodiments, the narrowed stiffer part that remains between the cut-outs has a width less than 40 mm, and preferably a width of 15-35 mm such that the part between the cut-outs will fit comfortably between the tendons in the narrowest part of a wearer's groin.

Moreover, the different elements shown in FIGS. 12*a-f* may be placed in any location in the Z-direction of the incontinence protector as herein described. The grooves need not be made from the topsheet side of the article. Accordingly, grooves made only in the absorbent core or from the backsheet side of the incontinence protector are also conceivable.

The invention claimed is:

1. A male incontinence protector having a longitudinal direction and a transverse direction, the incontinence protector comprising:
    a front end portion with a front end edge;
    a rear end portion with a rear end edge, the front end portion having greater maximum extension in the transverse direction than the maximum extension of the rear end portion in the transverse direction;
    side edges extending between the front end edge and the rear end edge;
    a garment-facing surface;
    a wearer-facing surface; and
    a tendon engagement member arranged in the rear end portion, the tendon engagement member having a maximum extension in the transverse direction of the incontinence protector of 40 mm to 70 mm and an extension in the longitudinal direction of the incontinence protector of 3 mm to 60 mm,
    wherein the side edges are generally tapered from the front end edge to the rear end edge such that the front end edge, the side edges, and the rear end edge of the incontinence protector form an essentially triangular shape.

2. The male incontinence protector according to claim 1, wherein the tendon engagement member is placed in a part of the rear end portion extending at least 3 mm and up to 70 mm from the rear end edge.

3. The male incontinence protector according to claim 2, wherein the tendon engagement member is arranged only in the part of the rear end portion extending at least 3 mm and up to 70 mm from the rear end edge.

4. The male incontinence protector according to claim 3, wherein when the incontinence protector is being worn by a wearer, the tendon engagement member is configured to be positioned between the legs of the wearer and the front end portion is configured to be positioned toward the abdomen of the wearer.

5. The male incontinence protector according to claim 1, wherein the tendon engagement member comprises at least one compressed groove.

6. The male incontinence protector according to claim 5, wherein the tendon engagement member comprises two intersecting compressed grooves.

7. The male incontinence protector according to claim 1, wherein the tendon engagement member comprises an absorbent or non-absorbent tendon abutment element.

8. The male incontinence protector according to claim 7, wherein the tendon abutment element is arranged on the wearer-facing surface.

9. The male incontinence protector according to claim 7, wherein the tendon abutment element is arranged on the garment-facing surface.

10. The male incontinence protector according to claim 7, wherein the tendon abutment element is placed between the garment-facing surface and the wearer-facing surface.

11. The male incontinence protector according to claim 7, wherein the tendon abutment element comprises a portion which is raised from surrounding portions of the wearing-facing surface of the rear end portion.

12. The male incontinence protector according to claim 1, wherein the incontinence protector comprises side edge shaping elements arranged along at least part of the side edges of the incontinence protector.

13. The male incontinence protector according to claim 12, wherein the side edge shaping elements comprise grooves at the wearer-facing side of the incontinence protector.

14. The male incontinence protector according to claim 12, wherein the side edge shaping elements comprise absorbent or non-absorbent elongate shaping elements extending along at least part of the side edges of the incontinence protector.

15. The male incontinence protector according to claim 12, wherein the side edge shaping elements are of the same type as the tendon engagement member in the rear end portion of the incontinence protector.

16. The male incontinence protector according to claim 15, wherein the incontinence protector comprises a coherent insert constituting side edge shaping elements and tendon engagement member, the coherent insert having a base portion placed in the rear end portion of the incontinence protector and two diverging leg portions extending along the side edges of the incontinence protector.

* * * * *